United States Patent
Fujisaki et al.

(10) Patent No.: US 9,737,383 B2
(45) Date of Patent: Aug. 22, 2017

(54) TRANSLUCENT ZIRCONIA SINTERED BODY AND ZIRCONIA POWDER, AND USE THEREFOR

(71) Applicant: TOSOH CORPORATION, Yamaguchi (JP)

(72) Inventors: Hiroyuki Fujisaki, Yamaguchi (JP); Kiyotaka Kawamura, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 15/104,036

(22) PCT Filed: Dec. 19, 2014

(86) PCT No.: PCT/JP2014/083763
§ 371 (c)(1),
(2) Date: Jun. 13, 2016

(87) PCT Pub. No.: WO2015/098765
PCT Pub. Date: Jul. 2, 2015

(65) Prior Publication Data
US 2016/0310245 A1    Oct. 27, 2016

(30) Foreign Application Priority Data
Dec. 24, 2013   (JP) ................................. 2013-265322

(51) Int. Cl.
| C04B 35/48 | (2006.01) |
| A61C 13/08 | (2006.01) |
| A61C 7/14 | (2006.01) |
| A61C 13/083 | (2006.01) |
| A61C 13/00 | (2006.01) |
| C04B 35/486 | (2006.01) |
| C04B 35/626 | (2006.01) |
| C01G 25/02 | (2006.01) |
| A61K 6/02 | (2006.01) |
| C04B 35/64 | (2006.01) |

(52) U.S. Cl.
CPC .............. *A61C 13/082* (2013.01); *A61C 7/14* (2013.01); *A61C 13/0022* (2013.01); *A61C 13/083* (2013.01); *A61K 6/024* (2013.01); *C01G 25/02* (2013.01); *C04B 35/486* (2013.01); *C04B 35/62695* (2013.01); *C04B 35/64* (2013.01); *A61C 2201/002* (2013.01); *C01P 2002/50* (2013.01); *C01P 2002/52* (2013.01); *C01P 2002/70* (2013.01); *C01P 2002/76* (2013.01); *C01P 2004/61* (2013.01); *C01P 2006/10* (2013.01); *C01P 2006/12* (2013.01); *C04B 2235/3217* (2013.01); *C04B 2235/3225* (2013.01); *C04B 2235/549* (2013.01); *C04B 2235/5409* (2013.01); *C04B 2235/602* (2013.01); *C04B 2235/608* (2013.01); *C04B 2235/72* (2013.01); *C04B 2235/77* (2013.01); *C04B 2235/96* (2013.01); *C04B 2235/9653* (2013.01)

(58) Field of Classification Search
CPC ..... C04B 35/48; C04B 35/482; C04B 35/484; C04B 35/486
See application file for complete search history.

(56) References Cited

U.S. PATENT DOCUMENTS

| 3,432,314 | A | * | 3/1969 | Lynch | .................... C04B 35/46 264/624 |
| 4,742,030 | A | * | 5/1988 | Masaki | ................. C04B 35/486 423/608 |
| 4,915,625 | A | * | 4/1990 | Tsukuma | ................ C04B 35/49 106/35 |
| 5,326,518 | A | * | 7/1994 | Kimura | .................... B28B 1/24 264/328.2 |
| 6,087,285 | A | * | 7/2000 | Oomichi | ............... C04B 35/486 501/103 |
| 7,806,694 | B2 | * | 10/2010 | Brodkin | ............ A61C 13/0006 106/35 |
| 2010/0003630 | A1 | † | 1/2010 | Yamashita | |

(Continued)

FOREIGN PATENT DOCUMENTS

| JP | 62-153163 | 7/1987 |
| JP | 2008-81325 | 4/2008 |

(Continued)

OTHER PUBLICATIONS

Chojiro Masuda, "Understanding Zirconia and Comprehensively Applying It to a Wide Dental Practice", Ann Jpn Prosthodont Soc 4, 2012, pp. 148-155, with English abstract.
Umberto Anselmi-Tamburini et al., "Transparent Nanometric Cubic and Tetragonal Zirconia Obtained by High-Pressure Pulsed Electric Current Sintering", Avd. Funct. Mater., 2007, 17, pp. 3267-3273.
International Search Report issued in Patent Application No. PCT/JP2014/083763, dated Jan. 27, 2015.

(Continued)

*Primary Examiner* — Noah Wiese
(74) *Attorney, Agent, or Firm* — Greenblum & Bernstein, P.L.C.

(57) ABSTRACT

To provide a zirconia sintered body having both excellent translucency and bending strength, specifically a zirconia sintered body having both translucency and strength suitable as a denture for front tooth, and a process for its production.

A translucent zirconia sintered body containing more than 4.0 mol % and at most 6.5 mol % of yttria and less than 0.1 wt % of alumina, and having a relative density of at least 99.82%, a total light transmittance of at least 37% and less than 40% to light with a wavelength of 600 nm at a thickness of 1.0 mm, and a bending strength of at least 500 MPa, and a process for its production.

13 Claims, No Drawings

(56) References Cited

U.S. PATENT DOCUMENTS

2011/0027742 A1    2/2011  Fujisaki et al.
2014/0227654 A1 †  8/2014  Fujisaki

FOREIGN PATENT DOCUMENTS

| | | | |
|---|---|---|---|
| JP | 2008081325 A | † | 4/2008 |
| JP | 2008-222450 | | 9/2008 |
| JP | 2008214168 A | † | 9/2008 |
| JP | 2008222450 A | † | 9/2008 |
| WO | 2008/013099 | | 1/2008 |
| WO | 2008013099 A1 | † | 1/2008 |
| WO | 2009/125793 | | 10/2009 |
| WO | 2013018728 A1 | † | 2/2013 |

OTHER PUBLICATIONS

International Preliminary Report on Patentability issued in Patent Application No. PCT/JP2014/083763, dated Jul. 7, 2016.

\* cited by examiner
† cited by third party

TRANSLUCENT ZIRCONIA SINTERED BODY AND ZIRCONIA POWDER, AND USE THEREFOR

TECHNICAL FIELD

The present invention relates to a zirconia sintered body having a high sintered body density and strength, and having a translucency which is very close to a natural tooth. This highly translucent zirconia sintered body is useful for dental applications, in particular for a front tooth, and is further suitable for use as a mill blank as a denture material, or as an orthodontic bracket.

BACKGROUND ART

A zirconia sintered body having a small amount of $Y_2O_3$ solid-solubilized as a stabilizing agent (hereinafter referred to as a "partially stabilized zirconia sintered body") has high strength and high toughness. Thus, such a partially stabilized zirconia sintered body is utilized for a mechanical structural material, such as a cutting tool, a die, a nozzle or a bearing. Further, it is utilized as a biomaterial such as a dental material, other than the mechanical structural material. In a case where a partially stabilized zirconia sintered body is to be used as a dental material, not only mechanical properties such as high strength and high toughness, but also optical characteristics such as translucency, color tone, etc. from the aesthetic point of view, are required.

From the aesthetic point of view, as zirconia having a translucency, a zirconia single crystal (cubic zirconia) containing about 10 mol % of yttria, has been utilized in e.g. ornaments. However, the zirconia single crystal has had a problem that its strength is extremely low.

On the other hand, a zirconia sintered body being a polycrystalline body of zirconia has no translucency. As a cause for this, it is known that pores existing in crystal grains and between crystal grains cause light scattering. Therefore, a study has heretofore been made to impart a translucency to a polycrystalline zirconia sintered body by reducing the pores, i.e. by increasing the sintered body density.

For example, Patent Document 1 discloses a zirconia sintered body which contains from 2 to 4 mol % of yttria and has an alumina content of at most 0.2 wt % and which has a total light transmittance of at least 35% at a thickness of 1 mm. However, the sintered body disclosed in Examples had a total light transmittance of 41%, which was 36% as a total light transmittance to light with a wavelength of 600 nm at a thickness of 1.0 mm. The sintered body was a sintered body having sufficient translucency and strength to be used as a denture for back tooth. On the other hand, the sintered body had a problem that the translucency was insufficient for use as a denture for front tooth.

Patent Document 2 discloses a zirconia sintered body containing from 1.5 to 5 mol % of yttria and having a porosity of at most 0.6%. However, the sintered body is a zirconia sintered body obtained by pressure sintering using hot isostatic pressing (hereinafter referred to as "HIP"), and with a zirconia sintered body obtained by pressureless sintering, sufficient translucency was not obtained.

Further, Patent Document 3 discloses a zirconia sintered body containing more than 4 mol % and at most 7 mol % of yttria, and having a total light transmittance of at least 40% at a wavelength of 600 nm at a thickness of 1 mm. This sintered body is also a zirconia sintered body obtained by pressure sintering using HIP, and with a zirconia sintered body obtained by pressureless sintering, sufficient translucency was not obtained.

Non-Patent Document 1 discloses a zirconia sintered body having transparency obtained by spark plasma sintering (hereinafter referred to as "SPS") of a zirconia powder containing 3 mol % of yttria and 8 mol % of yttria.

However, in order to use the zirconia sintered body disclosed in Patent Document 3 or Non-Patent Document 1 as a denture for front tooth, the transparency was too high and unnatural.

Further, in order to prepare a denture from a zirconia sintered body having a translucency, a method is known wherein a provisionally sintered green body is cut into a denture shape, followed by sintering it. In such a method, for example, a zirconia powder is subjected to usual press-molding to prepare a green body, and then the green body is provisionally sintered at temperatures of from 700 to 1,000° C., to prepare a mill blank. Then, by CAD/CAM, the prepared mill blank is carved into the shape of the denture, followed by sintering this. For example, the carved mill blank having the shape of the denture is sintered by using a process program such that it is heated to a sintering temperature at a temperature raising rate of 600° C./hr, and the retention time at the sintering temperature is set to be 2 hours, whereby the zirconia is sintered in a short time of about 7 hours.

On the other hand, in sintering by HIP, such sintering is conducted as primary sintering, and it is necessary to conduct HIP as sintering under pressure (secondary sintering), and, in SPS, sintering can be carried out in a short period of time and at a low temperature, but on the other hand, in SPS, a graphite mold is used, whereby heat treatment is required to make a sintered body colored by the material of the mold, to be colorless, by tempering the sintered body. Furthermore, it is necessary to cut a hard zirconia sintered body into the shape of a denture, and for such reasons, these methods are not practically employed. Therefore, it is desired to provide a zirconia powder, whereby a zirconia sintered body having a high density can be prepared by pressureless sintering in a short time.

PRIOR ART DOCUMENTS

Patent Documents

Patent Document 1: WO2009/125793
Patent Document 2: JP-A-62-153163
Patent Document 3: JP-A-2008-222450

Non-Patent Document

Non-patent Document 1: "Trabsparent Nanometric Cubic and Tetragonal Zirconia Obtained by High-Pressure Electric Current Sintering" Adv. Funct. Mater. 2007, 17, 3267-3273

DISCLOSURE OF INVENTION

Technical Problem

It is an object of the present invention to provide, by overcoming the above-mentioned disadvantages of conventional methods, a zirconia sintered body having excellent translucency with a high sintered body density, especially a zirconia sintered body having both translucency and strength suitable as a denture for front tooth, and to provide a zirconia powder, whereby such a zirconia sintered body can be produced by a simple process by pressureless sintering.

Solution to Problem

The present inventors have made a study for the above zirconia sintered body suitable as a denture for front tooth. As a result, they have found that a zirconia sintered body having its composition and physical properties controlled, has aesthetic properties comparable with natural front tooth.

Further, the present inventors have studied in detail the relationship between the yttria concentration and alumina concentration in the zirconia powder, and the sintered body density and the total light transmittance of the sintered body. As a result, they have found that in order to obtain a highly translucent zirconia sintered body suitable as a denture for front tooth by pressureless sintering, it is necessary not only to improve only the total light transmittance, but also to control the composition and physical properties of the zirconia powder and further their relationships, and thus have accomplished the present invention.

The gist of the present invention is as follows.

[1] A translucent zirconia sintered body characterized by containing more than 4.0 mol % and at most 6.5 mol % of yttria and less than 0.1 wt % of alumina, and having a relative density of at least 99.82%, a total light transmittance of at least 37% and less than 40% to light with a wavelength of 600 nm at a thickness of 1.0 mm, and a bending strength of at least 500 MPa.

[2] The translucent zirconia sintered body according to the above [1], which has a crystal grain size of from 0.3 to 1.0 μm.

[3] The translucent zirconia sintered body according to the above [1] or [2], wherein the ratio of the total light transmittance to D65 light at a sample thickness of 1.0 mm, to the total light transmittance to light with a wavelength of 600 nm at a sample thickness of 1.0 mm, is at least 1.16.

[4] A process for producing a translucent zirconia sintered body as defined in any one of the above [1] to [3], comprising a molding step of molding a zirconia powder containing more than 4.0 mol % and at most 6.5 mol % of yttria and less than 0.1 wt % of alumina, to obtain a green body, and a sintering step of sintering the green body under normal pressure at a sintering temperature of from 1,350° C. to 1,500° C.

[5] The process according to the above [4], wherein the density of the green body is more than 3.2 g/cm$^3$.

[6] A zirconia powder characterized by containing more than 4.0 mol % and at most 6.5 mol % of yttria and less than 0.1 wt % of alumina, and having a BET specific surface area of from 8 to 15 m$^2$/g.

[7] The zirconia powder according to the above [6], which has a crystallite size of from 320 to 380 Å.

[8] The zirconia powder according to the above [6] or [7], which has an average particle size of from 0.40 to 0.50 μm.

[9] The zirconia powder according to any one of the above [6] to [8], wherein the total proportion of tetragonal and cubic contained in the crystal is at least 80%.

[10] The zirconia powder according to any one of the above [6] to [9], which further contains an organic binder.

[11] The zirconia powder according to any one of the above [6] to [10], which is spray molded powder granules.

[12] A method for producing a zirconia sintered body, characterized by using the zirconia powder as defined in any one of the above [6] to [11].

[13] A dental material characterized by comprising the translucent zirconia sintered body as defined in any one of the above [1] to [3].

[14] The dental material according to the above [13], which is a denture, a denture mill blank, a denture for front tooth, a denture mill blank for front tooth, or an orthodontic bracket.

Advantageous Effects of Invention

According to the present invention, a zirconia sintered body having both translucency and strength suitable as a denture for front tooth is provided. The translucent zirconia sintered body of the present invention is excellent in translucency and is useful for dental applications, particularly as a zirconia sintered body to be used for a denture of front tooth. Further, it can be used also as a zirconia sintered body to be used as a mill blank as a denture material or as an orthodontic bracket.

Further, according to the zirconia powder of the present invention, it is possible to produce a zirconia sintered body having the translucency by pressureless sintering without using a large-scale pressure sintering apparatus for e.g. HIP.

DESCRIPTION OF EMBODIMENTS

The "stabilizer concentration" of the zirconia powder in the present invention refers to a value representing the ratio of stabilizer/(ZrO$_2$+stabilizer) by mol %.

The "additive content" refers to a value representing the ratio of additive/(ZrO$_2$+stabilizer+additive) by wt %.

The "relative density" is a proportion (%) of the measured density ($\rho$: g/cm$^3$) to the theoretical density ($\rho_0$: g/cm$^3$) and is a value determined by the following formula.

Relative density (%)=($\rho/\rho_0$)×100

Here, the measured density ($\rho$) is a value measured by the Archimedes method. Whereas, the theoretical density ($\rho_0$) is a value obtained by the following formula (1).

$$\rho_0=100/[(A/3.987)+(100-A)/\rho_X] \quad (1)$$

In the formula (1), $\rho_0$ is the theoretical density (g/cm$^3$), 3.987 is the theoretical density of alumina (g/cm$^3$), and $\rho_X$ is the theoretical density (g/cm$^3$) of a zirconia sintered body containing X mol % of yttria. Further, A is an alumina content (wt %) and is a weight percentage of alumina to the zirconia sintered body containing X mol % of yttria.

Further, when the yttria content or alumina content in the zirconia sintered body is different, $\rho_X$ in the formula (1) shows a different value. In the present invention, the theoretical density ($\rho_X$) of a zirconia sintered body wherein the content of yttria is the following mol % is set to have the following value.

Yttria content 3.0 mol %: $\rho_X$=6.095 g/cm$^3$

Yttria content 3.5 mol %: $\rho_X$=6.086 g/cm$^3$

Yttria content 4.0 mol %: $\rho_X$=6.080 g/cm$^3$

Yttria content 4.1 mol %: $\rho_X$=6.080 g/cm$^3$

Yttria content 4.5 mol %: $\rho_X$=6.072 g/cm$^3$

Yttria content 5.0 mol %: $\rho_X$=6.062 g/cm$^3$

Yttria content 5.5 mol %: $\rho_X$=6.052 g/cm$^3$

Yttria content 6.0 mol %: $\rho_X$=6.043 g/cm$^3$

Yttria content 6.5 mol %: $\rho_X$=6.033 g/cm³

Yttria content 7.4 mol %: $\rho_X$=6.019 g/cm³

Further, as $\rho_X$ in a zirconia sintered body having a yttria content other than the above, it is possible to use a value obtained by calculation from "Lattice Parameters and Density for $Y_2O_3$-Stabilized $ZrO_2$" J. Am. Ceram. Soc. 69 [4] 325-32 (1986).

The "crystallite size" is a value obtainable by the following formula (2) from an XRD peak (hereinafter referred to also as a "main XRD peak") of tetragonal (111) plane and cubic (111) plane in the powder X-ray diffraction (hereinafter referred to as "XRD") measurement.

$$\text{Crystallite size} = \kappa \lambda / \beta \cos \theta \quad (2)$$

In the formula (2), $\kappa$ is the Scherrer constant ($\kappa$=1), $\lambda$ is the wavelength of the X-ray used for the measurement ($\lambda$=1.541862 Å when the CuK$\alpha$ line is the radiation source), $\beta$ is the half-width of the main XRD peak, and $\theta$ is the Bragg angle of the main XRD peak.

Here, the main XRD peak is an XRD peak appearing in the vicinity of 2$\theta$=30.1 to 30.2° when the CuK$\alpha$ line is used as the radiation source. The peak is the XRD peak which tetragonal (111) plane and cubic (111) plane are overlapped. To calculate the crystallite size, the main XRD peak is subjected to waveform processing without conducting peak separation of the tetragonal and cubic. Then the Bragg angle ($\theta$) of the main XRD peak after the waveform processing and the half width ($\beta$) of the main XRD peak having its mechanical spread width corrected, are obtained.

The "average particle size" of a zirconia powder is a diameter of a sphere having the same volume as a particle having the median value of a cumulative curve of the particle size distribution represented by a volume basis (median diameter: a particle size corresponding to 50% of the cumulative curve). The average particle size is a value measured by a particle size distribution analyzer by a laser diffraction method.

The zirconia sintered body of the present invention contains yttria and alumina, wherein the content of yttria is more than 4.0 mol % and at most 6.5 mol % and the content of alumina is less than 0.1 wt %. The relative density of the sintered body is at least 99.82%; the bending strength thereof is at least 500 MPa; and the total light transmittance to light having a wavelength of 600 nm is at least 37% and less than 40% when the sample thickness is 1.0 mm.

The translucent zirconia sintered body of the present invention contains more than 4 mol % and at most 6.5 mol %, preferably at least 4.1 mol % and at most 6.0 mol %, more preferably at least 4.5 mol % and at most 6.0 mol %, of yttria which functions as a stabilizer. If the content of yttria is 4.0 mol % or less, translucency of the zirconia sintered body tends to be low. On the other hand, if it exceeds 6.5 mol %, translucency becomes too high. Therefore, in the case of using as a denture for front tooth, transparency tends to appear in the sintered body, and the denture for front tooth tends to have unnatural aesthetic properties. In addition, the strength tends to be too low, whereby it will not be tolerated for use as a denture for front tooth. Here, the content of yttria in the present invention can be obtained as a stabilizer concentration.

In the translucent zirconia sintered body of the present invention, the content of alumina is less than 0.1 wt %, preferably at most 0.08 wt %, further preferably at most 0.06 wt %. Alumina is contained as an additive in the translucent zirconia sintered body of the present invention. By containing alumina, the translucent zirconia sintered body of the present invention has high strength. On the other hand, if the alumina content is 0.1 wt % or more, translucency tends to be low, whereby aesthetic properties, as a denture for front tooth, tend to be unnatural. In order to have aesthetic properties suitable for a denture for front tooth, the content of alumina is preferably at most 0.05 wt %. Here, the content of alumina in the present invention can be obtained as an additive content. The content of alumina may be at least 0 wt % and less than 0.1 wt %, preferably at least 0 wt % and at most 0.05 wt %.

The translucent zirconia sintered body of the present invention has a relative density of at least 99.82%, preferably at least 99.85%. If the relative density is less than 99.82%, translucency of the zirconia sintered body tends to be low. Of the translucent zirconia sintered body of the present invention, the relative density is more preferably at least 99.90%, further preferably at least 99.95%.

Here, as mentioned above, the theoretical density, used for obtaining the relative density, has a different value depending on the yttria content or alumina content in the present invention. The following values are exemplified as the theoretical density of the translucent zirconia sintered body of the present invention.

TABLE 1

| $Y_2O_3$ content | $Al_2O_3$ content (wt %) | | |
|---|---|---|---|
| (mol %) | 0 | 0.05 | 0.08 |
| 3 | 6.095 | 6.093 | 6.092 |
| 3.5 | 6.086 | 6.084 | 6.083 |
| 4 | 6.080 | 6.078 | 6.077 |
| 4.1 | 6.080 | 6.078 | 6.077 |
| 4.5 | 6.072 | 6.070 | 6.070 |
| 5 | 6.062 | 6.060 | 6.060 |
| 5.5 | 6.052 | 6.050 | 6.050 |
| 6 | 6.043 | 6.041 | 6.041 |
| 6.5 | 6.033 | 6.032 | 6.031 |
| 7.4 | 6.019 | 6.017 | 6.017 |

Values in the Table are theoretical densities (g/cm³).

The translucent zirconia sintered body of the present invention is obtainable, without using pressure sintering such as HIP, by pressureless sintering. Further, by satisfying the above composition and by having a relative density of at least 99.82%, the total light transmittance to light with a wavelength of 600 nm at a sample thickness of 1.0 mm (hereinafter also referred to simply as the "total light transmittance") of at least 37% and less than 40% is satisfied.

The translucent zirconia sintered body of the present invention has the total light transmittance of at least 37% and less than 40%, preferably at least 37% and at most 39.9%, more preferably at least 37.1% and at most 39.5%. If the total light transmittance is 40% or more, such a sintered body tends to have transparency in addition to translucency. Since such a sintered body transmits light too much, it cannot be used as a denture for front tooth.

On the other hand, if the total light transmittance is less than 37%, coloration of the sintered body becomes too strong. If such a sintered body is used as a denture for front tooth, the front tooth tends to exhibit an unnatural color tone. When the total light transmittance is within the above range, the translucent zirconia sintered body of the present invention can be used, by itself, as a denture for front tooth without requiring a coating such as a glass coating. The total light transmittance is more preferably at least 37.3% and at most 39.2%, further preferably at least 37.3% and at most 39.0%, still more preferably at least 37.5% and at most 38.6% for the denture for front tooth not to require a coating.

In the translucent zirconia sintered body of the present invention, the ratio (hereinafter referred to as the "transmittance ratio") of the total light transmittance to D65 light at a sample thickness of 1.0 mm (hereinafter referred to as "D65 transmittance") to the total light transmittance, is preferably at least 1.16, more preferably at least 1.18. As the transmittance ratio becomes higher, aesthetic properties of the translucent zirconia sintered body of the present invention become closer to a natural front tooth, even if illuminated by light of different illumination containing a plurality of wavelengths, such as sunlight, fluorescent lamps, incandescent lamps, LED bulbs. Usually, the transmittance ratio of the translucent zirconia sintered body of the present invention is at most 1.4, preferably at most 1.35. In order to make a sintered body have aesthetic properties closer to a natural front tooth, the transmittance ratio is preferably from 1.16 to 1.4, more preferably from 1.16 to 1.35, further preferably from 1.18 to 1.35, still more preferably from 1.2 to 1.35, still further preferably from 1.25 to 1.35.

By having both of the above total light transmittance and transmittance ratio, the translucent zirconia sintered body of the present invention has aesthetic properties closer to a natural front tooth.

The D65 transmittance of the translucent zirconia sintered body of the present invention may have a value of satisfying the above transmittance ratio. The D65 transmittance of the translucent zirconia sintered body of the present invention may, for example, be preferably from 42% to 56%, more preferably from 42% to 54%, further preferably from 44% to 52%.

The translucent zirconia sintered body of the present invention has a bending strength of at least 500 MPa, preferably at least 550 MPa. The translucent zirconia sintered body of the present invention has proper translucency and a high relative density, and nevertheless, the bending strength is not too high. As the bending strength is at least 500 MPa, the strength satisfies for use as a denture for front tooth. In order to provide a strength suitable as a denture for front tooth, the bending strength is preferably at least 600 MPa, more preferably at least 650 MPa, further preferably at least 670 MPa, still more preferably at least 700 MPa.

The bending strength of the translucent zirconia sintered body of the present invention is usually at most 1,070 MPa, preferably at most 1,020 MPa, more preferably less than 1,000 MPa, further preferably at most 950 MPa, still more preferably at most 900 MPa.

As a denture for front tooth, the bending strength is, for example, preferably at least 500 MPa and at most 1,070 MPa, more preferably at least 500 MPa and less than 1,000 MPa, further preferably at least 550 MPa and less than 1,000 MPa, still more preferably at least 550 MPa and at most 950 MPa. Here, the bending strength is meant for a three-point bending strength.

The crystal grain size of the translucent zirconia sintered body of the present invention is preferably from 0.3 to 1.0 μm, more preferably from 0.3 to 0.9 μm, further preferably from 0.4 μm to 0.86 μm, still more preferably from 0.4 μm to 0.81 μm, still further preferably from 0.4 μm to 0.8 μm, whereby the relative density and bending strength will be excellent.

In the translucent zirconia sintered body of the present invention, the values or ranges of the yttria content, alumina content, relative density, total light transmittance, D65 transmittance, transmittance ratio, bending strength and crystal grain size, may be any combination of the above respective values.

The process for producing a translucent zirconia sintered body of the present invention may be a process which comprises a molding step of molding a zirconia powder containing more than 4.0 mol % and at most 6.5 mol % of yttria and less than 0.1 wt % of alumina, to obtain a green body, and a sintering step of sintering the green body under ordinary pressure at a sintering temperature of at least 1,350° C. and at most 1,500° C.

In the molding step, a zirconia powder containing more than 4.0 mol % and at most 6.5 mol % of yttria and less than 0.1 wt % of alumina, is molded to obtain a green body. So long as a green body having a desired shape is obtainable, the molding method is optional. The molding method may, for example, be press molding by uniaxial pressing, or CIP.

The density of the green body is preferably more than 3.2 g/cm$^3$, more preferably more than 3.2 g/cm$^3$ and at most 3.3 g/cm$^3$.

The zirconia powder to be subjected to the molding step is a zirconia powder containing more than 4.0 mol % and at most 6.5 mol % of yttria and less than 0.1 wt % of alumina. As a preferred zirconia powder to be subjected to the molding step (hereinafter referred to also as a "zirconia powder for the translucent zirconia sintered body of the present invention" or a "zirconia powder of the present invention"), the following zirconia powder may be mentioned.

By using the zirconia powder of the present invention, even if sintering in the sintering step is only by pressureless sintering, it is possible to obtain a zirconia sintered body of the present invention. Thus, in the sintering step, it is possible to obtain a translucent zirconia sintered body having both translucency and strength suitable as a denture for front tooth, without using pressure sintering such as HIP, or a special sintering method such as SPS.

The zirconia powder of the present invention is a zirconia powder which contains more than 4.0 mol % and at most 6.5 mol % of yttria, as a stabilizer, and wherein the content of alumina is less than 0.1 wt %.

The zirconia powder of the present invention contains more than 4.0 mol % and at most 6.5 mol %, preferably at least 4.1 mol % and at most 6.0 mol %, more preferably at least 4.5 mol % and at most 6.0 mol %, of yttria. Yttria functions as a stabilizer. If the stabilizer is 4.0 mol % or less, translucency of the obtainable zirconia sintered body tends to be too low.

On the other hand, if the stabilizer exceeds 6.5 mol %, a zirconia sintered body having translucency higher than the translucency required for a denture for front tooth, tends to be obtained. Therefore, when it is used as a denture for front tooth, transparency tends to appear, and the denture becomes unnatural. In addition, the strength tends to be too low, whereby it cannot be used as a denture for front tooth.

In the zirconia powder of the present invention, the content of alumina is less than 0.1 wt %, preferably at most 0.08 wt %, more preferably at most 0.06 wt %. As the zirconia powder of the present invention contains alumina, it is possible to obtain a translucent zirconia sintered body having strength suitable for use as a denture for front tooth.

On the other hand, if the alumina content is 0.1 wt % or more, translucency of the obtainable zirconia sintered body tends to be low, whereby the zirconia sintered body tends to have unnatural aesthetic properties as a denture for front tooth. In order to obtain a translucent zirconia sintered body having aesthetic properties suitable as a denture for front tooth, the content of alumina is preferably at most 0.05 wt %. The alumina content in the zirconia powder of the present invention is at least 0 wt % and less than 0.1 wt %, preferably at least 0 wt % and at most 0.05 wt %.

The crystallite size of the zirconia powder of the present invention is preferably from 320 to 380 Å, more preferably from 330 to 370 Å, further preferably from 340 to 360 Å, still more preferably from 350 to 360 Å, since the density of the obtainable zirconia sintered body tends to be high.

The zirconia powder of the present invention has a BET specific surface area of preferably from 8 to 15 m$^2$/g, more preferably from 10 to 15 m$^2$/g. With the BET specific surface area of at least 8 m$^2$/g, the zirconia powder tends to be a powder easily sinterable at a lower temperature. On the other hand, when the BET specific surface area is at most 15 m$^2$/g, preferably at most 14 m$^2$/g, the density of the obtainable sintered body tends to be less likely to be low, and a zirconia sintered body having translucency tends to be readily obtainable. In order to let a translucent zirconia sintered body having translucency and density suitable as a denture for front tooth be easily obtainable, the BET specific surface area is preferably at least 9 m$^2$/g and at most 15 m$^2$/g, more preferably at least 10 m$^2$/g and at most 14 m$^2$/g.

The zirconia powder of the present invention has both of the above crystallite size and BET specific surface area, whereby it is possible to provide a zirconia sintered body, by sintering only by pressureless sintering, more suitable as a denture for front tooth. That is, by pressureless sintering, without using a sintering method such as HIP or SPS, of a zirconia powder, mentioned above, having both of the above crystallite size and BET specific surface area, it becomes possible to readily obtain a translucent zirconia sintered body suitable as a denture for front tooth, particularly without necessity of coating treatment, etc, by itself.

In the zirconia powder of the present invention, the total proportion (hereinafter referred to also as "(T+C) phase ratio") of tetragonal and cubic contained in the crystal is preferably at least 80%, more preferably at least 85%. When the (T+C) phase ratio has such a value, it is possible to obtain a sintered body having both translucency and bending strength suitable as a denture for front tooth, even by sintering only by pressureless sintering. A preferred (T+C) phase ratio may be at least 90%, more preferably more than 90%, further preferably at least 95%.

In the present invention, the (T+C) phase ratio is a total proportion of tetragonal and cubic to the total of monoclinic, tetragonal and cubic in zirconia, and can be obtained from the following formula.

(T+C) phase ratio (%)=100−fm

In the above formula, fm is the monoclinic ratio (%). fm can be obtained from the following formula, using an XRD peak intensity corresponding to the monoclinic phase (111) plane (hereinafter referred to as "Im(111)"), an XRD peak intensity corresponding to the monoclinic phase (11-1) plane (hereinafter referred to as "Im(11-1)"), and an intensity of XRD peak corresponding to the tetragonal (111) plane and XRD peak corresponding to cubic (111) plane (hereinafter referred to as "It+c(111)".

fm (%)=[Im(111)+Im(11-1)]÷[Im(111)+Im(11-1)+It+c(111)]×100

Here, the XRD peak corresponding to the tetragonal (111) plane and the XRD peak corresponding to cubic (111) plane are an overlapped peak. It+c(111) is the intensity obtained by assuming them as one peak without separating them.

From the point of the ground time, moldability and sinterability, the average particle size of the zirconia powder of the present invention is preferably from 0.40 to 0.50 μm, more preferably from 0.40 to 0.45 μm, further preferably from 0.40 to 0.43 μm.

Further, the zirconia powder of the present invention is preferably spray molded powder granules (hereinafter simply referred to also as "granules").

The zirconia powder of the present invention is particularly preferably spray-granulated granules containing an organic binder in addition to yttria as a stabilizer and alumina as an additive. By the granules, the flowability for forming a green body tends to be high, and it is possible to form a green body excellent in shape retention after press molding. The average particle size of the granules is preferably from 30 to 80 μm, and the light-duty bulk density is from 1.10 to 1.40 g/cm$^3$. Here, the light-duty bulk density is a bulk density measured by a method in accordance with JIS R1628.

The organic binder may be at least one member selected from the group consisting of polyvinyl alcohol, polyvinyl butyrate, wax and an acrylic resin. Among these organic binders, an acrylic resin having a carboxy group or its derivative (e.g. a salt, particularly an ammonium salt) in the molecule is preferred. The acrylic resin may, for example, be at least one member selected from the group consisting of polyacrylic acid, polymethacrylic acid, an acrylic acid copolymer, a methacrylic acid copolymer, and derivatives thereof.

The amount of the organic binder to be added, is preferably from 0.5 to 10 wt %, particularly preferably from 1 to 5 wt %, to the zirconia powder in the zirconia powder slurry.

Thus, from the zirconia powder of the present invention, it is possible to obtain, by sintering only by pressureless sintering, zirconia sintered body having translucency suitable for a denture for a front tooth. That is, from the zirconia powder of the present invention, it is possible to obtain a zirconia sintered body having high translucency suitable for a denture for front tooth, even without using pressure sintering such as HIP treatment.

The density of the green body obtainable by molding the zirconia powder of the present invention may be more than 3.2 g/cm$^3$, preferably more than 3.2 g/cm$^3$ and at most 3.3 g/cm$^3$, more preferably more than 3.2 g/cm$^3$ and at most 3.27 g/cm$^3$. When the density of the green body is more than 3.2 g/cm$^3$, translucency of the obtainable sintered body tends to be suitable for a denture for front tooth. Further, when the density of the green body is at most 3.3 g/cm$^3$, the sintered body tends not to have defects to cause deterioration in strength. Further, with a green body of the zirconia powder of the present invention having the above (T+C) phase ratio, by sintering the green body, a proper sintering shrinkage proceeds. Then, it becomes easy to obtain a zirconia sintered body suitable for a denture for front tooth. The green body preferably has a (T+C) phase ratio of at least 90% and a density of green body of more than 3.2 g/cm$^3$ and at most 3.25 g/cm$^3$.

The zirconia powder of the present invention is preferably produced by e.g. a production process which comprises a raw material step of obtaining a hydrated zirconia sol by hydrolysis of a zirconium salt aqueous solution, a calcination step of drying and calcining the hydrated zirconia sol to obtain a calcined powder, and a grinding step of grinding the calcined powder to obtain a ground powder.

In the raw material step, a zirconium salt aqueous solution is hydrolyzed to obtain a hydrated zirconia sol. The zirconium salt aqueous solution to be used in the production of a hydrated zirconia sol, may be at least one of an aqueous solution selected from the group consisting of a mixture of zirconium hydroxide and an acid, zirconium oxychloride, zirconyl nitrate, zirconium chloride and zirconium sulfate.

In the case of obtaining the hydrated zirconia sol, it is preferred to add a yttria source to the zirconium salt aqueous solution before the hydrolysis or during the hydrolysis. The amount of the yttria source to be added, may be an amount comparable to the yttria content in the zirconia powder. The yttria source may be one which dissolves in the hydrated zirconium salt aqueous solution, and may be at least one selected from the group consisting of yttrium chloride, yttrium oxide, yttrium nitrate and yttrium hydroxide, or preferably at least either yttrium chloride or yttrium oxide.

In the calcination step, the obtained hydrated zirconia sol is dried to obtain a dried powder, then, the dried powder is calcined to obtain a calcined powder.

The drying in the calcination step may be conducted by an optional method, so long as moisture in the hydrated zirconia sol or residual water adhering to the hydrated zirconia sol, can be removed. The drying temperature may be exemplified to be from 160 to 200° C.

In the calcination step, the dried powder of the hydrated zirconia sol, obtained as described above, is calcined to obtain a calcined powder. The calcination temperature is preferably from 1,050 to 1,250° C., more preferably from 1,100 to 1,200° C. When the calcination temperature is within this range, not only aggregation of zirconia is prevented, but also, the particle size of the obtainable calcined powder tends to become uniform.

In the grinding step, the obtained calcined powder is ground. By the step, a zirconia powder of the present invention is obtained. In the grinding step, grinding is conducted until the average particle size of the calcined powder, obtained as described above, becomes to be from 0.40 to 0.50 µm. The grinding method is optional so long as it is a method whereby the calcined powder becomes to have the above average particle size. The grinding method may be at least either wet grinding or dry grinding, preferably wet grinding. A particularly preferred grinding method may be wet grinding using zirconia balls, and the zirconia balls preferably have a diameter of at most 3 mm.

Further, grinding is preferably conducted after addition of an alumina source to the calcined powder. Thus, zirconia and alumina are more uniformly mixed.

The alumina source, to be used as an additive, may be a compound of aluminum, and may, for example, be at least one selected from the group consisting of alumina, hydrated alumina, alumina sol, aluminum hydroxide, aluminum chloride, aluminum nitrate and aluminum sulfate, preferably at least one selected from the group consisting of alumina, hydrated alumina and alumina sol. At the time of grinding of the zirconia powder, an alumina source may be dispersed and mixed by adding and grinding a necessary amount of the alumina source.

The process for producing a zirconia powder of the present invention preferably further contain a granulation step. The zirconia powder of the present invention can thereby be made into granules. In the granulation step, the zirconia powder may be made into a slurry and spray-dried. The spray drying may, for example, be conducted by dropping the slurry in hot air of from 160 to 200° C. In the sintering step, a green body obtained in the molding step is sintered under atmospheric pressure at a sintering temperature of from 1,350 to 1,500° C. Whereby a translucent zirconia sintered body of the present invention can be obtained. The sintering temperature in the sintering step is preferably from 1,400° C. to 1,490° C., more preferably from 1,400° C. to 1,450° C.

The temperature-raising rate in the sintering step is at most 800° C./hour, preferably at most 600° C./hour. The retention time at the sintering temperature (hereinafter simply referred to also as "retention time") is depending upon the sintering temperature. The retention time in the sintering step may be exemplified at most 5 hours, preferably at most 3 hours, more preferably at most 2 hours.

The translucent zirconia sintered body of the present invention can be obtained by pressureless sintering. Here, the pressureless sintering is a method of sintering by simply heating without exerting an external force to the green body. Sintering under atmospheric pressure may be mentioned as specific pressureless sintering.

The sintering atmosphere may not be a reducing atmosphere, i.e. it may be any atmosphere other than a reducing atmosphere. The sintering atmosphere may be any oxygen atmosphere, and sintering in the atmospheric air is preferred. Sintering under atmospheric pressure at a temperature-raising rate of at most 600° C./hour at a sintering temperature of from 1,400° C. to 1,490° C., may be mentioned as a particularly preferred sintering step.

In the sintering step, it is preferred to conduct sintering only by pressureless sintering. Generally, as a means for improving translucency, it is common to use HIP or other pressure sintering, or a special sintering method such as SPS, after pressureless sintering. However, such pressure sintering or special sintering method makes not only the production process complex, but also the production cost increase. According to the production process of the present invention, particularly in the case of using the zirconia powder of the present invention, even by pressureless sintering only, it is possible to obtain a translucent zirconia sintered body having both sufficient translucency and strength as a denture for front tooth.

EXAMPLES

Now, the present invention will be described in detail with reference to Examples. However, the present invention is not limited to these Examples.

(Average Particle Size of Powder)

The average particle size of a zirconia powder was measured using a Microtrac particle size distribution analyzer (Model: 9320-HRA, manufactured by Honeywell). A powder slurry was suspended in distilled water and dispersed for 3 minutes, by means of an ultrasonic homogenizer (Model: US-150T, manufactured by NISSEI Corporation), as pretreatment conditions of a sample.

(Average Particle Size of Granules)

The average particle size of zirconia granules was obtained by a sieving test method in accordance with JIS Z 8801.

(BET Specific Surface Area)

The BET specific surface area of a powder sample was measured by nitrogen adsorption by a BET 1 point method. A common gas adsorption specific surface area measuring device (device name: TriStar 3000, manufactured by Micromeritics) was used as the measuring device. A powder sample was pre-treated by conducting deaeration treatment of heating at 250° C. for 60 minutes prior to the measurement.

(Identification of Crystal Phase)

The crystal phase was measured by powder X-ray diffraction measurement of the sample using a common X-ray diffraction apparatus (tradename: MXP-3, manufactured by Mac Science). The measurement conditions were as follows.

Radiation source: CuKα ray (A=1.541862 Å)
Measurement mode: step scanning
Scanning condition: 0.04° per second
Divergence slit: 1.00 deg
Scattering slit: 1.00 deg
Receiving slit: 0.30 mm
Measurement time: 3.0 seconds
Measurement range: 2θ=26° to 33°

From an XRD pattern obtained by the above XRD measurement, the (T+C) phase ratio was obtained by the following formula.

$$(T+C) \text{phase ratio } (\%) = 100 - fm$$

In the above formula, fm is the monoclinic crystal ratio (%), and it was obtained by the following formula.

$$fm\ (\%) = [Im(111) + Im(11\text{-}1)] \div [Im(111) + Im(11\text{-}1) + It+c(111)] \times 100$$

(Crystallite Size)

With respect to a powder sample, XRD measurement was conducted in the same manner as for identification of the crystal phase to obtain an XRD pattern. A half value width of a peak (main XRD peak) corresponding to tetragonal (111) plane and cubic (111) plane, was calculated from the obtained XRD pattern. The crystallite size was calculated by the following formula using the half value width. The half width was obtained by subjecting the measured results to background removal, followed by peak fitting processing using the X-ray diffraction apparatus.

$$\text{Crystallite size (Å)} = \kappa\lambda/(\beta \cos\theta)$$

In the above formula, κ is the Scherer constant (=1), and λ is λ of using CuKα ray as the radiation source, and is 1.541862 Å. Further, θ is the θ value of the main XRD peak, and is from 30.1 to 30.2°.

(Crystal Grain Size)

The crystal grain size of a zirconia sintered body is an average particle size calculated by a planimetric method from a SEM observation view obtained by means of a field emission scanning electron microscope (FESEM) (Model: JSM-T220, manufactured by JEOL Ltd.). A mirror-polished zirconia sintered body was used as a sample for the measurement, subjected to thermal etching treatment.

(Sintered Body Density)

The sintered body density was measured by the Archimedes' method.

(Total Light Transmittance)

The total light transmittance of a zirconia sintered body was measured by means of a spectrophotometer (Model: V-650, manufactured by JASCO Corporation). A disk-shaped sintered body having a thickness of 1 mm obtained by subjecting to double-side polishing was used as a sample. Light having a wavelength of from 220 to 850 nm was transmitted therethrough, whereby the light collected by an integrating sphere was measured.

(D65 Transmittance)

The total light transmittance with a D65 light source was measured in accordance with JIS K 7361 using a haze meter (Model: NDH2000, manufactured by Nippon Denshoku Industries Co., Ltd.). The same sample as used in the measurement of the total light transmittance was used in the measurement.

(Three-Point Bending Strength)

The strength of a zirconia sintered body was evaluated by a three-point bending measurement method, based on the method described in JIS R 1601.

Example 1

Preparation of Zirconia Powder

A zirconium oxychloride aqueous solution was hydrolyzed to obtain a hydrated zirconia sol. Yttrium chloride was added to the hydrated zirconia sol so that the yttria concentration would be 4.1 mol %, and then, the hydrated zirconia sol was dried at 180° C. The zirconia sol after drying, was fired at 1,120° C. for 2 hours. Thus, a zirconia calcined powder containing 4.1 mol % of yttria was obtained.

The obtained calcined powder was washed with distilled water and dried at 110° C. to obtain a zirconia water-washed powder. α-alumina was added to such a zirconia water-washed powder, so that the alumina content would be 0.05 wt %, to obtain a mixed powder.

A slurry was obtained by adding distilled water so that the solid content concentration of the mixed powder would be 45 wt %. The slurry was ground by ball mill using a ball mill having a diameter of 2 mm for 14 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C., and the obtained zirconia powder was evaluated. The evaluation results are shown in Table 2.

3 wt % of a polyacrylic acid-type organic binder was added to the ground slurry, and this mixture was dropped in hot air of 180° C. to carry out spray drying to obtain zirconia granules of this Example. The obtained zirconia granules had an average particle size of 50 μm and a light-duty bulk density of 1.25 g/cm³.

(Preparation of Sintered Body)

5 g of the obtained zirconia granules were put in a mold with a diameter of 25 mm and press-molded under a molding pressure of 19.6 MPa to obtain a primary green body. The obtained primary green body was subjected to CIP under a molding pressure of 196 MPa to obtain a green body. The obtained green body density is shown in Table 2.

The obtained green body was sintered under conditions of 1,450° C. at a temperature-raising rate of 600° C./hr and a retention time of 2 hours, to obtain a zirconia sintered body of this Example. The evaluation results of the obtained zirconia sintered body are shown in Table 3. The obtained zirconia sintered body had a total light transmittance of 37.3%. It is suitable for a denture for front tooth, since the total light transmittance is at least 37% and less than 40%.

Example 2

Preparation of Zirconia Powder

A zirconium oxychloride aqueous solution was hydrolyzed to obtain a hydrated zirconia sol. Yttrium chloride was added to the hydrated zirconia sol so that the yttria concentration would be 5.0 mol %, followed by drying this at 180° C. The zirconia sol after drying, was fired at 1,120° C. for 2 hours, whereby a zirconia calcined powder containing 5.0 mol % of yttria was obtained.

The obtained calcined powder was washed with distilled water and dried at 110° C. to obtain a zirconia water-washed powder. α-alumina was added to the zirconia water-washed powder, so that the alumina content would be 0.05 wt %, to obtain a mixed powder.

A slurry was obtained by adding distilled water so that the solid content concentration of the mixed powder would be 45 wt %. The slurry was ground by ball mill using a ball mill having a diameter of 2 mm for 17 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C., and the obtained zirconia powder was evaluated. The evaluation results are shown in Table 2.

3 wt % of a polyacrylic acid-type organic binder was added to the above ground slurry, and the mixture was dropped in hot air of 180° C. to carry out spray drying, to obtain zirconia granules of this Example. The obtained zirconia granules had an average particle size of 48 μm and a light-duty bulk density of 1.27 g/cm$^3$.

(Preparation of Sintered Body)

5 g of the obtained zirconia granules were put in a mold with a diameter of 25 mm and press-molded under a molding pressure of 19.6 MPa to obtain a primary green body. The obtained primary green body was subjected to CIP under a molding pressure of 196 MPa to obtain a green body. The obtained green body density is shown in Table 2.

The obtained green body was sintered under conditions of 1,450° C., at a temperature raising rate of 600° C./hr and a retention time of 2 hours, to obtain a zirconia sintered body of this Example. The evaluation results of the obtained zirconia sintered body are shown in Table 3. The obtained zirconia sintered body had a total light transmittance of 37.6%. It is suitable for a denture for front tooth, since the total light transmittance is at least 37% and less than 40%.

Example 3

Preparation of Zirconia Powder

A zirconium oxychloride aqueous solution was hydrolyzed to obtain a hydrated zirconia sol. Yttrium chloride was added to the hydrated zirconia sol so that the yttria concentration would be 6.0 mol %, followed by drying this at 180° C. The zirconia sol after drying, was fired at 1,120° C. for 2 hours, whereby a zirconia calcined powder containing 6.0 mol % of yttria was obtained.

The obtained calcined powder was washed with distilled water and dried at 110° C. to obtain a zirconia water-washed powder. α-alumina was added to the zirconia water-washed powder, so that the alumina content would be 0.05 wt %, to obtain a mixed powder.

A slurry was obtained by adding distilled water so that the solid content concentration of the mixed powder would be 45 wt %. The slurry was ground by ball mill using a ball mill having a diameter of 2 mm for 17 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C., and the obtained zirconia powder was evaluated. The evaluation results are shown in Table 2.

3 wt % of a polyacrylic acid-type organic binder was added to the above ground slurry, and the mixture was dropped in hot air of 180° C. to carry out spray drying, to obtain zirconia granules of this Example. The obtained zirconia granules had an average particle size of 48 μm and a light-duty bulk density of 1.26 g/cm$^3$.

(Preparation of Sintered Body)

5 g of the obtained zirconia granules were put in a mold with a diameter of 25 mm and press-molded under a molding pressure of 19.6 MPa to obtain a primary green body. The obtained primary green body was subjected to CIP under a molding pressure of 196 MPa to obtain a green body. The obtained green body density is shown in Table 2.

The obtained green body was sintered under conditions of 1,450° C., at a temperature raising rate of 600° C./hr and a retention time of 2 hours, to obtain a zirconia sintered body of this Example. The evaluation results of the obtained zirconia sintered body are shown in Table 3. The obtained zirconia sintered body had a total light transmittance of 38.5%. It is suitable for a denture for front tooth, since the total light transmittance is at least 37% and less than 40%.

Example 4

Preparation of Zirconia Powder

A zirconium oxychloride aqueous solution was hydrolyzed to obtain a hydrated zirconia sol. Yttrium chloride was added to the hydrated zirconia sol so that the yttria concentration would be 5.0 mol %, followed by drying this at 180° C. The zirconia sol after drying, was fired at 1,160° C. for 2 hours, whereby a zirconia calcined powder containing 5.0 mol % of yttria was obtained. The obtained calcined powder was washed with distilled water and dried at 110° C. to obtain a zirconia water-washed powder.

A slurry was obtained by adding distilled water so that the solid content concentration of the mixed powder would be 45 wt %. The slurry was ground by ball mill using a ball mill having a diameter of 2 mm for 25 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C., and the obtained zirconia powder was evaluated. The evaluation results are shown in Table 2.

3 wt % of a polyacrylic acid-type organic binder was added to the above ground slurry, and the mixture was dropped in hot air of 180° C. to carry out spray drying, to obtain zirconia granules of this Example. The obtained zirconia granules had an average particle size of 50 μm and a light-duty bulk density of 1.28 g/cm$^3$.

(Preparation of Sintered Body)

5 g of the obtained zirconia granules were put in a mold with a diameter of 25 mm and press-molded under a molding pressure of 19.6 MPa to obtain a primary green body. The obtained primary green body was subjected to CIP under a molding pressure of 196 MPa to obtain a green body. The obtained green body density is shown in Table 2.

The obtained green body was sintered under conditions of 1,450° C., at a temperature raising rate of 600° C./hr and a retention time of 2 hours, to obtain a zirconia sintered body of this Example. The evaluation results of the obtained zirconia sintered body are shown in Table 3. The obtained zirconia sintered body had a total light transmittance of 37.5%. It is suitable for a denture for front tooth, since the total light transmittance is at least 37% and less than 40%.

Example 5

Preparation of Zirconia Powder

A zirconium oxychloride aqueous solution was hydrolyzed to obtain a hydrated zirconia sol. Yttrium chloride was added to the hydrated zirconia sol so that the yttria concentration would be 5.5 mol %, followed by drying this at 180°

C. The zirconia sol after drying, was fired at 1,160° C. for 2 hours, whereby a zirconia calcined powder containing 5.5 mol % of yttria was obtained. The obtained calcined powder was washed with distilled water and dried at 110° C. to obtain a zirconia water-washed powder.

A slurry was obtained by adding distilled water so that the solid content concentration of the mixed powder would be 45 wt %. The slurry was ground by ball mill using a ball mill having a diameter of 2 mm for 22 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C., and the obtained zirconia powder was evaluated. The evaluation results are shown in Table 2.

3 wt % of a polyacrylic acid-type organic binder was added to the above ground slurry, and the mixture was dropped in hot air of 180° C. to carry out spray drying, to obtain zirconia granules of this Example. The obtained zirconia granules had an average particle size of 48 μm and a light-duty bulk density of 1.24 g/cm³.

(Preparation of Sintered Body)

5 g of the obtained zirconia granules were put in a mold with a diameter of 25 mm and press-molded under a molding pressure of 19.6 MPa to obtain a primary green body. The obtained primary green body was subjected to CIP under a molding pressure of 196 MPa to obtain a green body. The obtained green body density is shown in Table 2.

The obtained green body was sintered under conditions of 1,450° C., at a temperature raising rate of 600° C./hr and a retention time of 2 hours, to obtain a zirconia sintered body of this Example. The evaluation results of the obtained zirconia sintered body are shown in Table 3. The obtained zirconia sintered body had a total light transmittance of 39.2%. It is suitable for a denture for front tooth, since the total light transmittance is at least 37% and less than 40%.

Example 6

Preparation of Zirconia Powder

A zirconium oxychloride aqueous solution was hydrolyzed to obtain a hydrated zirconia sol. Yttrium chloride was added to the hydrated zirconia sol so that the yttria concentration would be 5.5 mol %, followed by drying this at 180° C. The zirconia sol after drying, was fired at 1,160° C. for 2 hours, whereby a zirconia calcined powder containing 5.5 mol % of yttria was obtained. The obtained calcined powder was washed with distilled water and dried at 110° C. to obtain a zirconia water-washed powder. α-alumina was added to the zirconia water-washed powder, so that the alumina content would be 0.05 wt %, to obtain a mixed powder.

A slurry was obtained by adding distilled water so that the solid content concentration of the mixed powder would be 45 wt %. The slurry was ground by ball mill using a ball mill having a diameter of 2 mm for 22 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C., and the obtained zirconia powder was evaluated. The evaluation results are shown in Table 2.

3 wt % of a polyacrylic acid-type organic binder was added to the above ground slurry, and the mixture was dropped in hot air of 180° C. to carry out spray drying, to obtain zirconia granules of this Example. The obtained zirconia granules had an average particle size of 43 μm and a light-duty bulk density of 1.26 g/cm³.

(Preparation of Sintered Body)

5 g of the obtained zirconia granules were put in a mold with a diameter of 25 mm and press-molded under a molding pressure of 19.6 MPa to obtain a primary green body. The obtained primary green body was subjected to CIP under a molding pressure of 196 MPa to obtain a green body. The obtained green body density is shown in Table 2. The obtained green body was sintered under conditions of 1,450° C., at a temperature raising rate of 600° C./hr and a retention time of 2 hours, to obtain a zirconia sintered body of this Example. The evaluation results of the obtained zirconia sintered body are shown in Table 3. The obtained zirconia sintered body had a total light transmittance of 37.5%. It is suitable for a denture for front tooth, since the total light transmittance is at least 37% and less than 40%.

Example 7

Preparation of Zirconia Powder

A zirconium oxychloride aqueous solution was hydrolyzed to obtain a hydrated zirconia sol. Yttrium chloride was added to the hydrated zirconia gel so that the yttria concentration would be 5.5 mol %, followed by drying this at 180° C. The zirconia gel after drying, was fired at 1,120° C. for 2 hours, whereby a zirconia calcined powder containing 5.5 mol % of yttria was obtained. The obtained calcined powder was washed with distilled water and dried at 110° C. to obtain a zirconia water-washed powder. α-alumina was added to the zirconia water-washed powder, so that the alumina content would be 0.05 wt %, to obtain a mixed powder.

A slurry was obtained by adding distilled water so that the solid content concentration of the mixed powder would be 45 wt %. The slurry was ground by ball mill using a ball mill having a diameter of 2 mm for 12 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C., and the obtained zirconia powder was evaluated. The evaluation results are shown in Table 2.

3 wt % of a polyacrylic acid-type organic binder was added to the above ground slurry, and the mixture was dropped in hot air of 180° C. to carry out spray drying, to obtain zirconia granules of this Example. The obtained zirconia granules had an average particle size of 48 μm and a light-duty bulk density of 1.24 g/cm³.

(Preparation of Sintered Body)

5 g of the obtained zirconia granules were put in a mold with a diameter of 25 mm and press-molded under a molding pressure of 19.6 MPa to obtain a primary green body. The obtained primary green body was subjected to CIP under a molding pressure of 196 MPa to obtain a green body. The obtained green body density is shown in Table 2. The obtained green body was sintered under conditions of 1,450° C., at a temperature raising rate of 600° C./hr and a retention time of 2 hours, to obtain a zirconia sintered body of this Example. The evaluation results of the obtained zirconia sintered body are shown in Table 3. The obtained zirconia sintered body had a total light transmittance of 37.5%. It is suitable for a denture for front tooth, since the total light transmittance is at least 37% and less than 40%.

Comparative Example 1

Zirconia Powder

A zirconia sintered body was prepared by using a zirconia powder (tradename: Zpex (registered trademark), manufactured by Tosoh Corporation) stabilized with 3.0 mol % of yttria and containing 0.05 wt % of $Al_2O_3$. The evaluation results of the zirconia powder are shown in Table 2.
(Preparation of Sintered Body)
The zirconia powder was put in a mold with a diameter of 25 mm and press-molded under a molding pressure of 19.6 MPa to obtain a primary green body. The obtained primary green body was CIP-molded under a pressure of 196 MPa, to obtain a green body.

Then, the green body was sintered under conditions of 1,450° C., at a temperature raising rate of 600° C./hr and a retention time of 2 hours, to obtain a zirconia sintered body of this Comparative Example. The evaluation results of the obtained zirconia sintered body are shown in Table 3.

The zirconia sintered body of this Comparative Example had a total light transmittance of 35.8% and a strength of 1,200 MPa. Thus, the zirconia sintered body of this Comparative Example was inferior in translucency as a denture for front tooth, while it had a strength suitable as a denture for back tooth.

Comparative Example 2

Preparation of Zirconia Powder

A zirconium oxychloride aqueous solution was hydrolyzed to obtain a hydrated zirconia sol. Yttrium chloride was added to the hydrated zirconia sol so that the yttria concentration would be 7.4 mol %, followed by drying this at 180° C. The hydrated zirconia sol after drying, was fired at 1,120° C. for 2 hours, whereby a zirconia calcined powder containing 7.4 mol % of yttria was obtained. The obtained calcined powder was washed with distilled water and dried at 110° C. to obtain a zirconia water-washed powder.

A slurry was obtained by adding distilled water so that the solid content concentration of the mixed powder would be 45 wt %. The slurry was ground by ball mill using a ball mill having a diameter of 2 mm for 18 hours so that the average particle diameter would be from 0.40 to 0.50 μm, to obtain a ground slurry. The average particle size of the obtained ground slurry was measured and taken as the average particle size of the zirconia powder. Further, a portion of the ground slurry was dried at 110° C.; and the obtained zirconia powder was evaluated. The evaluation results are shown in Table 2.

3 wt % of a polyacrylic acid-type organic binder was added to the above ground slurry, and the mixture was dropped in hot air of 180° C. to carry out spray drying, to obtain zirconia granules of this Example. The obtained zirconia granules had an average particle size of 45 μm and a light-duty bulk density of 1.24 $g/cm^3$.
(Preparation of Sintered Body)
5 g of the obtained zirconia granules were put in a mold with a diameter of 25 mm and press-molded under a molding pressure of 19.6 MPa to obtain a primary green body. The obtained primary green body was subjected to CIP under a pressure of 196 MPa to obtain a green body. The obtained green body density is shown in Table 2.

The obtained green body was sintered under conditions of 1,450° C., at a temperature raising rate of 600° C./hr and a retention time of 2 hours, to obtain a zirconia sintered body of this Comparative Example. The evaluation results of the obtained zirconia sintered body are shown in Table 3. The obtained zirconia sintered body had a total light transmittance of 36.7%. Thus, the zirconia sintered body of this Comparative Example was inferior in translucency as a denture for front tooth, since the total light transmittance was low.

Comparative Example 3

Zirconia Powder

A zirconia sintered body was prepared by using a zirconia powder (tradename: TZ-4YS, manufactured by Tosoh Corporation) stabilized with 4.0 mol % of yttria. The evaluation results of the zirconia powder are shown in Table 2.
(Preparation of Sintered Body)
The zirconia powder was put in a mold with a diameter of 25 mm and press-molded under a molding pressure of 19.6 MPa to obtain a primary green body. The obtained primary green body was subjected to CIP under a pressure of 196 MPa, to obtain a green body. The obtained green body density is shown in Table 2.

The obtained green body was sintered under conditions of 1,550° C., at a temperature raising rate of 600° C./hr and a retention time of 2 hours, to obtain a sintered body of this Comparative Example. The evaluation results of the obtained zirconia sintered body are shown in Table 3.

The zirconia sintered body of this Comparative Example had a total light transmittance of 36.0%. Thus, the zirconia sintered body of this Comparative Example was inferior in translucency as a denture for front tooth, since the total light transmittance was low.

Comparative Example 4

Zirconia Powder

A zirconia sintered body was prepared by using a zirconia powder (tradename: TZ-5YS, manufactured by Tosoh Corporation) stabilized with 5.0 mol % of yttria. The evaluation results of the zirconia powder are shown in Table 2.
(Preparation of Sintered Body)
The zirconia powder was put in a mold with a diameter of 25 mm and press-molded under a molding pressure of 19.6 MPa to obtain a primary green body. The obtained primary green body was subjected to CIP under a pressure of 196 MPa, to obtain a green body. The obtained green body density is shown in Table 2.

The obtained green body was sintered under conditions of 1,550° C., at a temperature raising rate of 600° C./hr and a retention time of 2 hours, to obtain a sintered body of this Comparative Example. The evaluation results of the obtained zirconia sintered body are shown in Table 3.

The zirconia sintered body of this Comparative Example had a total light transmittance of 36.0%. Thus, the zirconia sintered body of this Comparative Example was inferior in translucency as a denture for front tooth, since the total light transmittance was low.

Comparative Example 5

Zirconia Powder

A zirconia sintered body was prepared by using a zirconia powder (tradename: TZ-6YS, manufactured by Tosoh Corporation) stabilized with 6.0 mol % of yttria. The evaluation results of the zirconia powder are shown in Table 2.
(Preparation of Sintered Body)

The zirconia powder was put in a mold with a diameter of 25 mm and press-molded under a molding pressure of 19.6 MPa to obtain a primary green body. The obtained primary green body was subjected to CIP under a pressure of 196 MPa, to obtain a green body. The obtained green body density is shown in Table 2. The green body was sintered under conditions of 1,500° C., at a temperature raising rate of 600° C./hr and a retention time of 2 hours, to obtain a sintered body of this Comparative Example. The evaluation results of the obtained zirconia sintered body are shown in Table 3.

The zirconia sintered body of this Comparative Example had a total light transmittance of 25.3%. Thus, the zirconia sintered body of this Comparative Example was inferior in translucency as a denture for front tooth, since the total light transmittance was low, and is not suitable for a denture for front tooth.

From the zirconia powder used in this Comparative Example, it was not possible to obtain a zirconia sintered body having high translucency by pressureless sintering only.

Comparative Example 6

The same zirconia powder as in Comparative Example 5 was molded in the same manner as in Comparative Example 5, to obtain a green body. The obtained green body was sintered under the conditions of 1,550° C., at a temperature raising rate of 600° C./hr and a retention time of 2 hours, to obtain a sintered body of this Comparative Example. The evaluation results of the obtained zirconia sintered body are shown in Table 3.

The zirconia sintered body of this Comparative Example had a total light transmittance of 24.5%. Thus, the zirconia sintered body of this Comparative Example was inferior in translucency as a denture for front tooth, since the total light transmittance was low.

From the zirconia powder used in this Comparative Example, it was not possible to obtain a zirconia sintered body having high translucency by pressureless sintering only.

TABLE 2

|  | $Y_2O_3$ (mol %) | $Al_2O_3$ (wt %) | BET (m$^2$/g) | (T + C) phase ratio (%) | Crystallite size (Å) | Average particle size (μm) | Green body density (g/cm$^3$) |
|---|---|---|---|---|---|---|---|
| Example 1 | 4.1 | 0.05 | 12.9 | 86 | 340 | 0.40 | 3.24 |
| Example 2 | 5.0 | 0.05 | 13.6 | 96 | 350 | 0.40 | 3.23 |
| Example 3 | 6.0 | 0.05 | 12.8 | 98 | 360 | 0.42 | 3.21 |
| Example 4 | 5.0 | 0 | 11.7 | 96 | 350 | 0.43 | 3.24 |
| Example 5 | 5.5 | 0 | 9.8 | 97 | 360 | 0.44 | 3.26 |
| Example 6 | 5.5 | 0.05 | 9.7 | 97 | 360 | 0.43 | 3.27 |
| Example 7 | 5.5 | 0.05 | 11.9 | 97 | 350 | 0.45 | 3.25 |
| Comparative Example 1 | 3.0 | 0.05 | 12.5 | 63 | 340 | 0.43 | 3.23 |
| Comparative Example 2 | 7.4 | 0 | 13.3 | 99 | 350 | 0.43 | 3.20 |
| Comparative Example 3 | 4.0 | 0 | 6.9 | 84 | 360 | 0.54 | 2.63 |
| Comparative Example 4 | 5.0 | 0 | 6.7 | 99 | 410 | 0.52 | 2.64 |
| Comparative Example 5 | 6.0 | 0 | 6.3 | 94 | 390 | 0.52 | 2.69 |
| Comparative Example 6 | 6.0 | 0 | 6.3 | 94 | 390 | 0.52 | 2.69 |

TABLE 3

|  | $Y_2O_3$ (mol %) | Sintering temp. (° C.) | Sintered body density (g/cm$^3$) | Theoretical density (g/cm$^3$) | Relative density (%) | Crystal grain size (μm) | 600 nm transmitance (%) | D65 transmitance (%) | Transmitance ratio | Strength (MPa) |
|---|---|---|---|---|---|---|---|---|---|---|
| Example 1 | 4.1 | 1450 | 6.076 | 6.078 | 99.97 | 0.41 | 37.3 | 44 | 1.18 | 870 |
| Example 2 | 5.0 | 1450 | 6.058 | 6.060 | 99.97 | 0.49 | 37.6 | 47 | 1.25 | 770 |
| Example 3 | 6.0 | 1450 | 6.039 | 6.041 | 99.97 | 0.86 | 38.5 | 52 | 1.35 | 550 |
| Example 4 | 5.0 | 1450 | 6.053 | 6.062 | 99.85 | 0.49 | 37.5 | 48 | 1.28 | 670 |
| Example 5 | 5.5 | 1450 | 6.049 | 6.052 | 99.95 | 0.81 | 39.2 | 50 | 1.28 | 655 |
| Example 6 | 5.5 | 1450 | 6.046 | 6.050 | 99.93 | 0.80 | 37.5 | 49 | 1.31 | 635 |
| Example 7 | 5.5 | 1450 | 6.046 | 6.050 | 99.93 | 0.80 | 37.5 | 49 | 1.31 | 615 |
| Comparative Example 1 | 3.0 | 1450 | 6.087 | 6.093 | 99.90 | 0.41 | 35.8 | 41 | 1.15 | 1200 |
| Comparative Example 2 | 7.4 | 1450 | 6.013 | 6.019 | 99.90 | — | 36.7 | 45 | 1.23 | 310 |
| Comparative Example 3 | 4.0 | 1550 | 6.070 | 6.080 | 99.84 | — | 36.0 | 42 | 1.17 | 1150 |

TABLE 3-continued

|  | Y$_2$O$_3$ (mol %) | Sintering temp. (° C.) | Sintered body density (g/cm$^3$) | Theoretical density (g/cm$^3$) | Relative density (%) | Crystal grain size (μm) | 600 nm transmitance (%) | D65 transmitance (%) | Transmitance ratio | Strength (MPa) |
|---|---|---|---|---|---|---|---|---|---|---|
| Comparative Example 4 | 5.0 | 1550 | 6.049 | 6.062 | 99.79 | — | 36.0 | 43 | 1.19 | 800 |
| Comparative Example 5 | 6.0 | 1500 | 6.011 | 6.043 | 99.47 | — | 25.3 | 28 | 1.11 | — |
| Comparative Example 6 | 6.0 | 1550 | 6.004 | 6.043 | 99.36 | — | 24.5 | 27 | 1.10 | 490 |

*In the Table, "—" represents "not measured".

INDUSTRIAL APPLICABILITY

The translucent zirconia sintered body of the present invention can be used as a denture, including a denture for front tooth. Further, it can be used as a dental material such as a denture mill blank, an orthodontic bracket, etc.

The entire disclosure of Japanese Patent Application No. 2013-265322 filed on Dec. 24, 2013 including specification, claims, drawings and summary is incorporated herein by reference in its entirety.

The invention claimed is:

1. A translucent zirconia sintered body containing more than 4.0 mol % and at most 6.5 mol % of yttria and less than 0.1 wt % of alumina, and having a relative density of at least 99.82%, a total light transmittance of at least 37% and less than 40% to light with a wavelength of 600 nm at a thickness of 1.0 mm, a crystal grain size of from 0.3 to 1.0 μm, and a bending strength of at least 500 MPa.

2. The translucent zirconia sintered body according to claim 1, wherein a ratio of total light transmittance to D65 light at a sample thickness of 1.0 mm, to total light transmittance to light with a wavelength of 600 nm at a sample thickness of 1.0 mm, is at least 1.16.

3. A process for producing a translucent zirconia sintered body as defined in claim 1, comprising molding a zirconia powder containing more than 4.0 mol % and at most 6.5 mol % of yttria and less than 0.1 wt % of alumina, to obtain a green body, and sintering the green body under normal pressure at a sintering temperature of from 1,350° C. to 1,500° C.

4. The process according to claim 3, wherein the density of the green body is more than 3.2 g/cm$^3$.

5. A zirconia powder containing more than 4.0 mol % and at most 6.5 mol % of yttria and less than 0.1 wt % of alumina, and having a crystallite size of from 320 to 380 Å, and a BET specific surface area of from 8 to 15 m$^2$/g.

6. The zirconia powder according to claim 5, having an average particle size of from 0.40 to 0.50 μm.

7. The zirconia powder according to claim 5, wherein the total proportion of tetragonal and cubic contained in the crystal is at least 80%.

8. The zirconia powder according to claim 5, further containing an organic binder.

9. The zirconia powder according to claim 5, wherein the zirconia powder is spray molded powder granules.

10. A method for producing a zirconia sintered body, comprising forming a body from the zirconia powder as defined in claim 5, and sintering the formed body.

11. A dental material comprising the translucent zirconia sintered body as defined in claim 1.

12. The dental material according to claim 11, which is a denture, a denture mill blank, a denture for front tooth, a denture mill blank for front tooth, or an orthodontic bracket.

13. A process for producing a translucent zirconia sintered body containing more than 4.0 mol % and at most 6.5 mol % of yttria and less than 0.1 wt % of alumina, and having a relative density of at least 99.82%, a total light transmittance of at least 37% and less than 40% to light with a wavelength of 600 nm at a thickness of 1.0 mm, and a bending strength of at least 500 MPa, the process comprising molding a zirconia powder containing more than 4.0 mol % and at most 6.5 mol % of yttria and less than 0.1 wt % of alumina, to obtain a green body having a density of more than 3.2 g/cm$^3$, and sintering the green body under normal pressure at a sintering temperature of from 1,350° C. to 1,500° C.

* * * * *